(12) United States Patent
Gogineni et al.

(10) Patent No.: US 12,311,045 B2
(45) Date of Patent: *May 27, 2025

(54) NATURAL NON-SULFATE RINSE-OFF CLEANSING COMPOSITIONS WITH HIGH OIL LOADING, AND METHODS OF USE

(71) Applicant: L'OREAL, Paris (FR)

(72) Inventors: Aditi Gogineni, Hoboken, NJ (US); Heather Lee, Wayne, NJ (US); Kyle Robbins, Toms River, NJ (US)

(73) Assignee: L'OREAL, Paris (FR)

( * ) Notice: Subject to any disclaimer, the term of this patent is extended or adjusted under 35 U.S.C. 154(b) by 601 days.

This patent is subject to a terminal disclaimer.

(21) Appl. No.: 16/916,544

(22) Filed: Jun. 30, 2020

(65) Prior Publication Data

US 2021/0401716 A1 Dec. 30, 2021

(51) Int. Cl.

| | |
|---|---|
| A61K 8/60 | (2006.01) |
| A61K 8/31 | (2006.01) |
| A61K 8/37 | (2006.01) |
| A61K 8/41 | (2006.01) |
| A61K 8/44 | (2006.01) |
| A61K 8/46 | (2006.01) |
| A61K 8/73 | (2006.01) |
| A61Q 5/02 | (2006.01) |
| A61Q 5/12 | (2006.01) |

(52) U.S. Cl.
CPC .............. *A61K 8/604* (2013.01); *A61K 8/416* (2013.01); *A61K 8/44* (2013.01); *A61K 8/463* (2013.01); *A61K 8/737* (2013.01); *A61Q 5/02* (2013.01); *A61Q 5/12* (2013.01); *A61K 2800/34* (2013.01)

(58) Field of Classification Search
CPC .......... A61K 8/604; A61K 8/463; A61K 8/44; A61K 8/737; A61K 8/416; A61K 2800/34; A61Q 5/12; A61Q 5/02
See application file for complete search history.

(56) References Cited

U.S. PATENT DOCUMENTS

| | | | |
|---|---|---|---|
| 8,865,147 B2* | 10/2014 | Rizk .................. | A61K 8/731 |
| | | | 424/70.19 |
| 9,216,147 B2 | 12/2015 | Fahl et al. | |
| 9,724,283 B2* | 8/2017 | Rizk .................. | A61Q 5/02 |
| 10,265,261 B2 | 4/2019 | Park et al. | |
| 10,398,637 B2 | 9/2019 | Lee et al. | |
| 11,096,878 B2* | 8/2021 | Botto ................. | A61K 8/345 |
| 2008/0008672 A1 | 1/2008 | Tobita | |
| 2018/0116937 A1 | 5/2018 | Park et al. | |
| 2019/0262246 A1 | 8/2019 | Liang et al. | |
| 2019/0314258 A1 | 10/2019 | Laurent et al. | |
| 2019/0365622 A1 | 12/2019 | Botto et al. | |
| 2019/0365623 A1 | 12/2019 | Botto et al. | |

FOREIGN PATENT DOCUMENTS

| | | | |
|---|---|---|---|
| EP | 2768474 B1 | 4/2017 | |
| WO | 2013057045 A2 | 4/2013 | |
| WO | 2015044056 A1 | 4/2015 | |
| WO | 2015044057 A1 | 4/2015 | |
| WO | 18002557 A1 | 1/2018 | |
| WO | 2019/000394 A1 | 1/2019 | |
| WO | 2019/104398 A1 | 6/2019 | |
| WO | WO-2019/168917 A1 | 9/2019 | |
| WO | WO-2019232128 A1 * | 12/2019 | ............ A61K 8/416 |
| WO | WO-2019232134 A1 * | 12/2019 | ............ A61K 8/345 |

OTHER PUBLICATIONS

Preliminary Search Report and Written Opinion issued on Aug. 26, 2020 for corresponding French Application No. FR2008690.
Database GNPD; Mintel; "Repair Damage Ritual Set," 2018 XP055806286.
Database GNPD; Mintel; "Shampoo," 2020 XP055806217.
Database GNPD; Mintel; "Shampoo & Wash," 2017 XP055806314.
International Search Report and Written Opinion issued on Oct. 12, 2021 for corresponding PCT Application No. PCT/US2021/038659.

* cited by examiner

*Primary Examiner* — Jeffrey T. Palenik
(74) *Attorney, Agent, or Firm* — POLSINELLI PC

(57) ABSTRACT

The present disclosure relates to natural non-sulfate rinse-off rinse-off cleansing compositions with high oil load, methods of use and making. The cleansing compositions include: (a) up to 20 wt. % of one or more anionic surfactants selected from acyl taurates, acyl glutamates, acyl isethionates, salts thereof, and mixtures thereof; (b) one or more nonionic surfactants comprising alkyl polyglucosides; (c) one or more amphoteric surfactants; (d) one or more oil-based conditioning agents selected from squalane, glyceryl esters, natural oils, esters other than glyceryl esters, and mixtures thereof; and (e) one or more thickening agents. The cleansing compositions are particularly useful for cleansing hair.

19 Claims, No Drawings

NATURAL NON-SULFATE RINSE-OFF CLEANSING COMPOSITIONS WITH HIGH OIL LOADING, AND METHODS OF USE

FIELD OF THE DISCLOSURE

The present disclosure relates to sulfate free rinse-off cleansing compositions, and methods of use, particularly shampoo compositions, that include high oil loads. The shampoo compositions and methods are particularly useful for cleaning and conditioning hair.

BACKGROUND

Typically, "dirt" contains traces of oil and grease that stick to the surface of skin and hair. Rinsing with only water is not sufficient to adequately remove the oil and grease, as a result cleansing compositions are typically required. Surfactants are one of the main functional ingredients used in cleansing compositions. Surfactants interact with water, thereby allowing it to "wet" surfaces more efficiently. The surfactant-water combination is then capable of surrounding the dirt particles and carrying them away during rinsing. Agitation of the water solution, for example by rubbing hands together during washing or lathering shampoo into hair, further facilitates in the process of removing dirt.

Conventional cleansing compositions such as shampoos, for example, contain surfactants in varying amounts. Typically, anionic surfactants are utilized because they provide foaming to cleansing compositions and provide a deep cleaning effect. Sulfates are an example of an anionic surfactant that are frequently utilized in shampoos for its lathering effect in effectively removing dirt and oil from hair. However, the use of sulfates in shampoo has been questioned, with some believing that sulfates may cause damage to certain hair types, skin irritation and averse to overall health. Particularly, those with sensitive skin or hair, skin conditions such as rosacea, or who have allergies may have an adverse reaction if repeatedly exposed to sulfate in shampoo. Additionally, sulfates may strip color from color treated hair. Consequently, sulfate-free shampoo is frequently recommended.

Sulfate-free shampoos frequently utilize sarcosinate surfactants. Sarcosinates, including sodium lauryl sarcosinate and sodium lauroyl sarcosinate for example, is derived from sarcosine and is used as a foaming and cleansing agent in shampoo.

Nonionic surfactants may also be included to provide cleansing, solubilizing, and dispersing properties, and are usually less irritating than anionic surfactants. Nonionic surfactants, however, often exhibit less foaming ability and do not provide any enhancement to viscosity (e.g., often times the composition is thinner and runnier with increased amounts of nonionic surfactants). Higher viscosity is desired for some cleansing applications, particularly for product handling or ease of application. In addition, higher viscosity personal care products are generally more aesthetically appealing to many consumers.

There remains a need in the art for a sarcosinate free, sulfate-free shampoo formulation that delivers cosmetic benefits to the hair, while also providing desirable performance and feel properties. Further, there remains a need in the art for a naturally derived sarcosinate free, sulfate-free shampoo composition that foams and cleanses well, with desired "thickness" (viscosity) that is mild to the skin and hair. The cleansing compositions should also rinse away from the body with ease. Often, the addition of a particular component to a cleansing composition will enhance one desired property to the detriment of another desired property. It is therefore difficult to achieve a perfect balance of desirable performance properties.

SUMMARY OF THE DISCLOSURE

The present invention is directed to naturally derived sarcosinate free, sulfate-free rinse-off cleansing compositions, particularly shampoo compositions, using a combination of sulfate-free anionic surfactants together with other surfactants and oil-based conditioning agents that allow high/concentrated oil loading to deliver high cosmetic benefits. Natural, biodegradable and renewable components are used in the sarcosinate free, sulfate-free composition, exhibiting high stability and ease to processing. Sarcosinate-free (higher stability and easier processing), sulfate free rinse-off cleaning compositions of the subject invention provide a safe, environmentally friendly product, having high cosmeticity particularly beneficial for use with normal to extremely damaged hair, providing both cleansing and conditioning properties.

Rinse-off cleansing compositions of the subject invention have a high oil load, that include a high concentration of a combination of surfactants and oil-based, preferably naturally derived, conditioning agent(s), along with natural thickening agents. Conventional hair cleansing compositions, particularly shampoos, are formulated with a high percentage of water, which in turn reduces the amount of cleansing and conditioning agents in the compositions. The term "concentrated" herein, or "high", when referring to the oil-based conditioners generally means a high level or high weight percent of oil-based conditioning agents as a total weight percent of the composition. Typically, shampoo compositions do not include non-pre-emulsified oils, and instead generally utilize pre-emulsified oils or silicone conditioning agents. For the subject composition, the oil load is preferably up to about 5% from oil-based conditioning agents, preferably being non-silicone, that are not pre-emulsified oils in the composition, wherein the composition is a shampoo. In the subject invention, the process involves mixing the oil-based conditioning agents without pre-emulsification of the oils.

The rinse off cleansing compositions of the instant case have a high oil load, or oil load of about 5%. The sarcosinate-free, sulfate-free natural high oil-based cleansing compositions of the subject invention perform better than traditional cleansing compositions, such as shampoos. Compared to traditional sulfate-free shampoos, the subject shampoo provides a natural sulfate-free shampoo that has a higher oil load than traditional shampoos, to provide a high load oil-based shampoo that conditions the hair, without weighing the hair down, to achieve superior results compared to the traditional shampoos.

Obtaining a high/concentrated oil load rinse-off cleansing composition is not as simple as merely increasing the total amount of surfactants and conditioning agents in a composition. A concentrated/high oil load rinse-off cleansing composition that is effective, stable, having a pleasing texture, while at the same time providing a natural sulfate-free, sarcosinate-free cleansing composition is difficult to obtain. The inventors discovered a unique balance of surfactants systems of varying ionicities that can be used in high concentrations with oil-based conditioning agents and natural thickeners to form surprisingly effective cleansing compositions that are robust, stable, and safe, have pleasant rheological properties, are safe, natural and provide concentrated conditioning to the hair. The high oil load cleansing compositions provide, for example, good foaming, lather, distribution, detangling, shine, smoothness, discipline, and improved shaping to hair.

Although the amounts of surfactants and high/concentrated oil load are higher than typically used in traditional shampoos, the cleansing compositions of the instant case do not "weigh down" the hair, which is the opposite of what was expected. Rather, the compositions impart desirable styling properties to the hair, such as smoothness, detangling, and shine, without requiring use of silicones. Silicones are often included in traditional cleansing compositions to provide these types of styling benefits to hair. The subject compositions utilize natural polymers and oil-based conditioning agents, and preferably does not contain or require any synthetic polymers, silicones, or secondary gums for structuring. Furthermore, the cleansing compositions of the instant case provide hair with desirable styling properties without requiring use of film forming polymers. Film forming polymers are commonly used to provide style benefits, such as styling hold and shaping memory. Film forming polymers (including anionic, amphoteric, and nonionic film-forming polymers) may optionally be included in the instant cleansing compositions but are certainly not required and may be excluded.

A unique balance of different surfactants of varying ionicities have been utilized in achieving the subject sarcosinate free, sulfate-free shampoo, providing a high oil load to form surprisingly effective cleansing compositions that are natural, robust, stable, and safe, and have pleasant rheological properties. The sarcosinate free, sulfate-free shampoo compositions provide, for example, good foaming, lather, distribution, detangling, moisture, and conditioning properties to the hair.

One aspect of the invention provides a rinse-off cleansing composition with high oil load comprising:
  (a) up to 20 wt. % of one or more anionic surfactants selected from acyl taurates, acyl glutamates, acyl isethionates, salts thereof, and mixtures thereof;
  (b) one or more nonionic surfactants comprising one or more alkyl polyglucosides (APG);
  (c) one or more amphoteric surfactants;
  (d) one or more oil-based conditioning agents selected from squalane, glyceryl esters, and mixtures thereof;
  (e) one or more thickening agents;
  wherein all wt. % are based on total wt. of the cleansing composition.

Preferably, the APG to the one or more oil conditioning agent of the cleaning composition has a ratio greater than 1. More preferably, the APG to the one or more oil conditioning agent ranges from about 3 up to about 60. Most preferably, the APG to the one or more oil conditioning agent ranges from about 5 up to about 20. Preferably, the APG is selected from lauryl glucoside, octyl glucoside, decyl glucoside, coco glucoside, and mixtures thereof. The one or more amphoteric surfactants are preferably selected from betaines, alkyl sultaines, alkyl amphoacetates, alkyl amphoproprionates, and mixtures thereof.

The one or more anionic surfactants preferably comprises at least one acyl taurate and optionally at least one acyl isethionate. Alternatively, the anionic surfactants comprise at least one acyl taurate, acyl isethionate, and acyl glutamate. In an aspect of the invention, the one or more anionic surfactants are selected from sodium cocoyl taurate, sodium methyl cocoyl taurate, sodium cocoyl isethionate, disodium cocoyl glutamate, sodium cocoyl glutamate, sodium stearoyl glutamate, and mixtures thereof. The one or more conditioning agents are preferably selected from squalane, glyceryl esters, natural-oil fragrances, esters, and mixtures thereof. The thickening agent is a natural thickening agent, preferably being cationic guar.

Concentrated/high oil load is achieved as the oil-based conditioning agents total oil loading preferably ranges from about 0.2% to about 5 wt. %. More preferably, the total oil loading ranges from about 0.3% to about 5 wt. %. Most preferably, the total oil loading ranges from about 0.5% to about 4 wt. %. The cleansing composition preferably is essentially free of carboxylate surfactants comprising sarcosinates and/or essentially free of sulfate-based surfactants, salts thereof, and/or essentially free of non-natural oil-based conditioning agents and/or essentially free of silicones and/or essentially free of non-natural thickening agents. The term "substantially free" or "essentially free" as used herein, with respect to sarcosinates, sulfate-based surfactants, salts thereof, non-natural oil-based conditioning agents, silicones, and/or non-natural thickening agents, means that there is less than about 5% by weight of these specific material added to a composition (i.e. not part of a raw material added to the composition), based on the total weight of the compositions. Nonetheless, the compositions may include less than about 4 wt. %, 3 wt. %, 2 wt. %, 1 wt. %, less than about 0.5 wt. %, less than about 0.1 wt. %, or none of the specified materials.

Another aspect of the invention provides a rinse-off cleansing composition with high oil load, the composition comprising:
  a. up to 20 wt. % of one or more anionic surfactants selected from acyl taurate, acyl isethionate, acyl glutamate, salts and mixtures thereof;
  b. about 5% to 30 wt. % of one or more nonionic surfactants comprising alkyl polyglucosides (APG);
  c. about 2% to 25 wt. % of one or more amphoteric surfactants;
  d. about 0.2% to 5% of one or more oil-based conditioning agents selected from squalane, glyceryl esters, esters, and mixtures thereof;
  e. about 0.5% to 5% of one or more thickening agents comprising natural thickening agents;
  f. about 25% to 75% water;
  wherein all weight percentages are based on the total weight of the cleansing composition.

In yet another aspect of the invention, the cleansing composition comprises: about 1% to 5 wt. % of acyl taurate; about 1% to 10 wt. % of acyl isethionate; optionally, about 0.1% to 3 wt. % of acyl glutamate; about 7% to 20 wt. % of APG; about 2% to 12 wt. % of one or more of one or more betaines; about 0.2% to 5% of one or more oil conditioning agents selected from squalane, glyceryl esters, esters, and mixtures thereof; about 0.5% to 5% of one or more thickening agents comprising cationic guar; wherein all weight percentages are based on the total weight of the cleansing composition.

A method for treating hair comprising contacting hair with the rinse-off cleansing composition is also provided. In one aspect, the method for cleansing the hair and/or scalp, the method comprising applying to the hair and/or scalp, and subsequently rinsing off, a rinse-off cleansing composition with high oil load comprises: (a) up to 20 wt. % of one or more anionic surfactants selected from acyl taurates, acyl glutamates, acyl isethionates, salts thereof, and mixtures thereof; (b) one or more nonionic surfactants comprising one or more alkyl polyglucosides (APG); (c) one or more amphoteric surfactants; (d) one or more oil-based conditioning agents selected from squalane, glyceryl esters, and mixtures thereof; (e) one or more thickening agents.

A process of making a rinse-off cleansing composition with high oil load, is also provided. The process includes the steps of mixing a solution comprising: i. up to 20 wt. % of one or more anionic surfactants selected from acyl taurates, acyl glutamates, acyl isethionates, salts thereof, and mixtures thereof; ii. one or more nonionic surfactants comprising one or more alkyl polyglucosides (APG); iii. one or more amphoteric surfactants; iv. one or more oil-based conditioning agents selected from squalane, glyceryl esters, natural oils, esters other than glyceryl esters, and mixtures thereof; and v. one or more thickening agents. The process also includes the step of adjusting pH of the solution. The oil-based conditioning agents are not pre-emulsified. All weight percentages are based on the total weight of the cleansing composition.

The cleansing compositions of the instant disclosure are particularly useful for cleansing and conditioning hair. The compositions exhibit good cleansing ability, lather, foaming and foam stability, and conditioning properties. Additionally, the cleansing compositions provide a variety of desirable styling benefits to the hair, for example, smoothness, detangling, and shine. Accordingly, the cleansing compositions may be used in methods for cleansing hair, methods of conditioning hair, and methods for imparting smoothness, detangling, and/or shine to hair.

DETAILED DESCRIPTION OF THE DISCLOSURE

In one aspect, the formula is composed of at least one anionic surfactant containing taurate surfactants, glutamate surfactants, and isethionate surfactants, at least one oil-based conditioning agent such as squalene, glyceryl esters such as glyceryl oleate, natural-oil fragrances, and optionally, esters, and/or derivatives thereof, nonionic surfactant such as alkyl polyglycoside (APG), an amphoteric surfactant, and thickeners such as cationic guar.

Preferably, the at least one anionic sulfate free surfactant has a range of about 1%-30%, where preferably the maximum contribution sodium cocoyl isethionate ranges from about 1-10%. The composition may further comprise a total level of nonionic surfactants ranging from about 5-30% with a combination of alkyl polyglucoside, preferably ranging from about 7-20%. An amphoteric surfactant such as betaine may be utilized in the composition, preferably having a level of about 3-12%.

Total oil loading preferably ranges from about 0.5% to 5%. In one embodiment, the system preferably utilizes only one natural polymer, preferably comprising cationic guar. A synergistic relationship between APG, optionally decyl glucoside, and glyceryl oleate results, with preferably a ratio of at least 3:1 up to 60:1, to achieve viscosity and cosmetic performance. In addition, this synergistic level of non-ionic surfactant to glyceryl oleate enables the suspension of oils and optionally pearlizing agent in the formulation.

The formulation does not contain or require any synthetic polymers, silicones, or secondary gums for structuring.

A combination of different surfactants are utilized, including anionic, nonionic, and amphoteric (zwitterionic) surfactants. Anionic surfactants carry a negative charge on the polar head group. These surfactants are typically used for their detergency properties. They are highly effective at removing dirt and oil from the hair and scalp. Nonionic surfactants are those that have no (or very little) residual electric charge. These surfactants can perform a variety of functions, such as emulsion stabilization, mild detergency and viscosity modification. Amphoteric (zwitterionic) surfactants are dual-charged (have both a positive and negative charge on the molecule). Many amphoteric surfactants display pH-dependent charge behavior, having one charge at a lower pH and the opposite charge at a higher pH. These types of surfactants tend to be mild both to skin and hair. They can also provide foam-boosting properties in combination with anionic surfactants, which enhances lather. The combination of surfactants in the instant disclosure, in high concentrations, provides the cleansing compositions with cleansing power, stabilizing properties, viscosity enhancement, and foaming.

The surfactants of the instant disclosure include: (i) one or more anionic surfactants; (ii) one or more alkyl polyglucosides; and (iii) one or more amphoteric surfactants. The surfactants may also optionally include: (iv) additional miscellaneous nonionic surfactants.

The subject rinse-off cleansing composition with high oil load comprises a surfactants including: a. up to 20 wt. % of one or more anionic surfactants selected from acyl taurates, acyl glutamates, acyl isethionates, salts thereof, and mixtures thereof; b. one or more nonionic surfactants comprising one or more alkyl polyglucosides (APG); and c. one or more amphoteric surfactants. Additionally, the composition includes one or more oil-based conditioning agents selected from squalane, glyceryl esters, and mixtures thereof, and one or more thickening agents.

Preferably, the process of making the rinse-off cleansing composition with high oil load includes the steps of preparing and mixing a solution including: i. up to 20 wt. % of one or more anionic surfactants selected from acyl taurates, acyl glutamates, acyl isethionates, salts thereof, and mixtures thereof; ii. one or more nonionic surfactants comprising one or more alkyl polyglucosides (APG); iii. one or more amphoteric surfactants; iv. one or more oil-based conditioning agents selected from squalane, glyceryl esters, natural oils, esters other than glyceryl esters, and mixtures thereof; and v. one or more thickening agents. pH adjustment of the solution is carried out, if needed, to a pH range of about 4.5 to about 6, preferably pH range of about 5.0 to about 5.5. The oil-based conditioning agents are preferably not pre-emulsified. All weight percentages are based on the total weight of the cleansing composition.

In one aspect, the process is carried out by: preparing an SK solution (side kettle/SK) of thickening agents plus water; and preparing a MK solution (main kettle/MK) including the steps of: 1) mixing APG with water; 2) adjusting the pH, ranging from about 5.0 to about 5.6, and heat; 3) add oil-based conditioning agents; 4) add one or more anionic surfactants forming a homogeneous solution; 5) Add SK solution and continue cooling; 7) add surfactants and oil-based conditioning agents; 8) add amphoteric surfactant/s; and 9) pH, ranging from about 5.0 to about 5.6.

Surfactants

The total amount of surfactants of the surfactants ranges from about 15 to about 65 wt. %, based on the total weight of the cleansing composition. In some instances, the total amount of surfactants of the surfactant system ranges from about 15 to about 60 wt. %, about 15 to about 55 wt. %, about 15 to about 50 wt. %, about 20 to about 60 wt. %, from about 20 to about 55 wt. %, from about 20 to about 50 wt. %, from about 25 to about 65 wt. %, from about 25 to about 60 wt. %, from about 25 to about 55 wt. %, or from about 25 to about 50 wt. %, based on the total weight of the cleansing composition.

Useful but non-limiting examples of surfactants that may be used are provided below.

(i) Non-Sulfate Anionic Surfactants

The compositions of the present disclosure comprise one or more non-sulfate anionic surfactants selected from acyl taurates, acyl glutamates, acyl isethionates, salts thereof, and mixtures thereof. Most preferably, the one or more non-sulfate anionic surfactants selected from acyl taurates, acyl glutamates, acyl isethionates, salts thereof, and mixtures thereof are present in an amount of up to 20% wt. of In some instances, the non-sulfate anionic surfactant(s) selected from acyl taurates, acyl glutamates, acyl isethionates, salts thereof, and mixtures thereof are the predominant type of surfactants used (i.e., there is a higher percentage of non-sulfate anionic surfactant(s) than any other single surfactant type in the cleansing composition). Moreover, in some instances, the total amount of non-sulfate anionic surfactant is not more than about 20 wt. %, and may be higher than the total amount of all other surfactant types including the alkyl polyglucosides, amphoteric surfactants, and nonionic surfactants. In other words, the phrase "all other surfactants" means any and all surfactants in the cleansing composition other than anionic surfactants.

The total amount of non-sulfate anionic surfactants in the cleansing compositions can vary but typically ranges from about 5 to about 30 wt. %, preferably, not more than about 20 wt. %, based on the total weight of the cleansing composition.

The total amount of non-sulfate anionic surfactant(s) to the total amount of all other surfactants [amphoteric plus nonionic of the composition may be about 0.4:1 to about 1:1, about 0.5:1 to about 0.9:1, about 0.6:1 to about 0.8:1, about 0.7:1 to about 0.8:1. Preferably, the total amount of anionic surfactants is less than the total amount of all other surfactants, at about 0.4:1, 0.5:1, 0.6:1, 0.7:1, 0.75:1, 0.8:1, 0.9:1, 1:3, 1:1.5. Most preferably, the anionic surfactant does not exceed 20 wt. % of the total composition.

Acyl Isethionates

Non-limiting examples of useful acyl isethionates include those of formula (I) and (II):

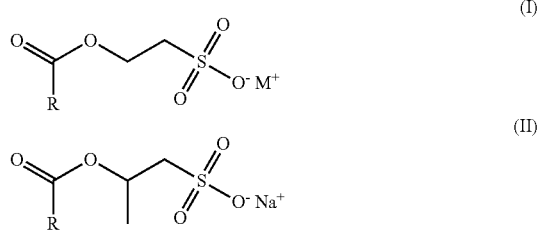

wherein R, R1, R2 and R3 are each independently selected from H or an alkyl chain having 1-24 carbon atoms, said chain being saturated or unsaturated, linear or branched, and X is COO— or SO3—. Sodium is shown as the cation in formula (VI) but the cation for both formula (V) and formula (VI) may be an alkali metal ion such as sodium or potassium, ammonium ions, or alkanolammonium ions such as monoethanolammonium or triethanolammonium ions. Non-limiting examples of acyl isethionates include sodium isethionate, sodium cocoyl isethionate, sodium lauroyl methyl isethionate, and sodium cocoyl methyl isethionate.

By way of non-limiting example, suitable acyl isethionate surfactants may include the reaction product of fatty acids esterified with isethionic acid and neutralized with sodium hydroxide. For example, acyl isethionates surfactants may be prepared by the reaction of an isethionate salt such as metal or ammonium isethionate and an a saturated or unsaturated, straight or branched, alkyl or alkenyl chain fatty acid having from 6 to 30 carbon atoms, preferably from 8 to 22 carbon atoms, more preferably from 6 to 18 carbon atoms. Optionally, a mixture of aliphatic fatty acids may be used for the preparation of commercial fatty acyl isethionates surfactants. Suitable fatty acids for isethionate surfactants can be derived from coconut oil or palm kernel oil, for instance.

Non-limiting examples of acyl isethionate surfactants that may be used include sodium lauroyl isethionate, sodium lauroyl methyl isethionate, sodium oleoyl isethionate, sodium oleoyl methyl isethionate, sodium stearoyl isethionate, sodium stearoyl methyl isethionate, sodium myristoyl isethionate, sodium myristoyl methyl isethionate, sodium palmitoyl isethionate, sodium palmitoyl methyl isethionate, sodium cocoyl isethionate, sodium cocoyl methyl isethionate, a blend of stearic acid and sodium cocoyl isethionate, ammonium cocoyl isethionate, ammonium cocoyl methyl isethionate, and mixtures thereof.

The total amount of isethionate surfactants may range up to about 15%, such as from about 4% to about 15% by weight, relative to the total weight of the rinse-off composition. For example, the total amount of isethionate surfactants may range from about 4% to about 14%, about 4% to about 13%, about 4% to about 12%, about 4% to about 11%, about 4% to about 10%, about 4% to about 9%, about 4% to about 8%, about 4% to about 7%, about 4% to about 6%, about 5% to about 15%, about 5% to about 14%, about 5% to about 13%, about 5% to about 12%, about 5% to about 11%, about 5% to about 10%, about 5% to about 9%, about 5% to about 8%, about 5% to about 7%, about 6% to about 15%, about 6% to about 14%, about 6% to about 13%, about 6% to about 12%, about 6% to about 11%, about 6% to about 10%, about 6% to about 9%, about 6% to about 8%, about 7% to about 15%, about 7% to about 14%, about 7% to about 13%, about 7% to about 12%, about 7% to about 11%, about 7% to about 10%, about 7% to about 9%, about 8% to about 15%, about 8% to about 14%, about 8% to about 13%, about 8% to about 12%, about 8% to about 11%, about 8% to about 10%, about 9% to about 15%, about 9% to about 14%, about 9% to about 13%, about 9% to about 12%, about 9% to about 11%, about 10% to about 15%, about 10% to about 14%, about 10% to about 13%, about 10% to about 12%, about 11% to about 15%, about 11% to about 14%, about 1% to about 13%, about 12% to about 15%, about 12% to about 14%, or about 13% to about 15% by weight, relative to the total weight of the rinse-off composition, including ranges and sub-ranges there between.

In various embodiments, the total amount of acyl isethionate(s) in the cleansing composition, if present, may vary but is typically from about 0.01 to about 25 wt. %, based on the total weight of the anionic surfactant. In some instance, the total amount of acyl isethionate(s) in the cleansing composition is from about 0.01 to about 20 wt. %, about 0.01 to about 15 wt. %, about 0.01 to about 10 wt. %, about 0.01 to about 5 wt. %, about 0.1 to about 25 wt. %, about 0.1 to about 20 wt. %, about 0.1 to about 15 wt. %, or about 0.1 to about 10 wt. %, or about 0.1 to about 5 wt. %, based on the total weight of the anionic surfactant. Preferably, the acyl isethionate(s) ranges from about 0.01% to about 15%, more preferably about 0.05% to 12%, and most preferably about 1% to 10 wt. % of the total weight of the cleaning composition, preferably being sodium cocoyl isethionate. Alternatively, the acyl isethionate(s) are not more than 10 wt. % of the anionic surfactants.

Acyl Amino Acids (Amino Acid Surfactants)

The one or more non-sulfate anionic surfactants of the present invention may also include acyl amino acids or amino acid surfactants. Such surfactants are typically based on alanine, arginine, aspartic acid, glycine, isoleucine, leucine, lysine, phenylalanine, serine, tyrosine, valine, sarcosine, threonine, glutamic acid, and taurine.

The most common cation associated with the acyl amino acid can be sodium or potassium. Alternatively, the cation can be an organic salt such as triethanolamine (TEA) or a metal salt. Non-limiting examples of useful acyl amino acids include those of the general formula (III):

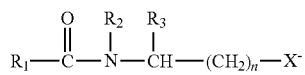

(III)

wherein R, R1, R2 and R3 are each independently selected from H or an alkyl chain having 1-24 carbon atoms, said chain being saturated or unsaturated, linear or branched, and X is COO— or SO3—.

Acyl Taurates

Acyl Taurates are of the acyl amino acid surfactant type. Non-limiting examples of acyl taurates include those of formula (IV):

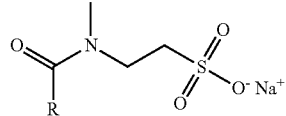

(IV)

wherein R, R1, R2 and R3 are each independently selected from H or an alkyl chain having 1-24 carbon atoms, or from 6-20 carbon atoms, or from 8 to 16 carbon atoms, said chain being saturated or unsaturated, linear or branched, and X is COO— or SO3—. Non-limiting examples of acyl taurate salts include sodium cocoyl taurate and sodium methyl cocoyl taurate.

The total amount of acyl taurate(s) in the cleansing composition, if present, may vary but is typically from about 0.01 to about 33 wt. %, based on the total weight of the cleansing composition. In some instance, the total amount of acyl taurate(s) in the cleansing composition is from about 0.01 to about 20 wt. %, about 0.01 to about 15 wt. %, about 0.01 to about 10 wt. %, about 0.01 to about 5 wt. %, about 0.1 to about 25 wt. %, about 0.1 to about 20 wt. %, about 0.1 to about 15 wt. %, or about 0.1 to about 10 wt. %, or about 0.1 to about 5 wt. %, based on the total weight of the cleaning composition. Preferably, acyl taurate ranges from about 0.01 to 10 wt. %, more preferably 0.1 to about 7 wt. %, and most preferably 1 to 5 wt. % of the total weight of the cleaning composition.

Acyl Glutamates

Acyl glutamates are of the acyl amino acid surfactant type. Non-limiting examples of useful acyl glutamates include those of formula (V):

(V)

wherein R is an alkyl chain of 8 to 16 carbon atoms. Sodium is shown as the cation in the above formula (XI) but the cation may be an alkali metal ion such as sodium or potassium, ammonium ions, or alkanolammonium ions such as monoethanolammonium or triethanolammonium ions. Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

The total amount of acyl glutamates in the cleansing composition, if present, may vary but is typically from about 0.01 to about 33 wt. %, based on the total weight of the anionic surfactant. In some instance, the total amount of acyl glutamates in the cleansing composition is from about 0.01 to about 20 wt. %, about 0.01 to about 15 wt. %, about 0.01 to about 10 wt. %, about 0.01 to about 5 wt. %, about 0.1 to about 25 wt. %, about 0.1 to about 20 wt. %, about 0.1 to about 15 wt. %, or about 0.1 to about 10 wt. %, or about 0.1 to about 5 wt. %, based on the total weight of the anionic surfactant. Preferably, acyl glutamates ranges from about 0.01 to 10 wt. %, more preferably 0.05 to about 7 wt. %, and most preferably 0.1% to 3 wt. % of the total weight of the cleaning composition. The acyl glutamates are optional, and preferably is one of disodium cocoyl glutamate, sodium cocoyl glutamate, sodium stearoyl glutamate, and mixtures thereof.

Other Non-Sulfate Anionic Surfactants

The compositions of the present disclosure may further comprise other non-sulfate anionic surfactants. Other useful non-sulfate anionic surfactants include, but are not limited to, alkyl sulfonates, alkyl sulfosuccinates, alkyl sulfoacetates, alkoxylated monoacids, other acyl amino acids such as acyl glycinates, acyl sarcosinates, salts thereof, and a mixture thereof. Non-limiting examples of these other useful non-sulfate anionic surfactants are provided below.

Alkyl Sulfonates

Useful alkyl sulfonates include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenvlalkanesulfonates, alpha-olefinsulfonates, olefin sulfonates, alkene sulfonates, hydroxyalkanesulfonates and disulfonates, secondary alkane-sulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (VI) is particularly useful.

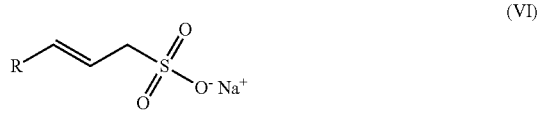

(VI)

R is selected from H or alkyl chain that has 1-24 carbon atoms, preferably 6-24 carbon atoms, more preferably, 8 to 20 carbon atoms, said chain being saturated or unsaturated, linear or branched. Sodium is shown as the cation in the above formula (III) but the cation may be an alkali metal ion such as sodium or potassium, ammonium ions, or alkanolammonium ions such as monoethanolammonium or triethanolammonium ions. In some instances, the alkyl sulfonate(s) are selected from C8-C16 alkyl benzene sulfonates, C10-C20 paraffin sulfonates, C10-C24 olefin sulfonates, salts thereof, and mixtures thereof. C10-C24 olefin sulfonates are particularly preferred. A non-limiting but particularly useful example of a C10-C24 olefin sulfonate that can be used in the instant compositions is sodium C14-16 olefin sulfonate.

The total amount of alkyl sulfonate(s) in the cleansing compositions, if present, may range from about 1 to about 40 wt. %, based on the total weight of the cleansing composition. In some cases, the total amount of alkyl sulfonate(s) in the cleansing compositions may range from about 1 to about 35 wt. %, about 1 to about 30 wt. %, about 1 to about 25 wt. %, about 5 to about 35 wt. %, about 5 to about 30 wt. %, about 5 to about 25 wt. %, about 10 to about 40 wt. %, about 10 to about 35 wt. %, about 10 to about 30 wt. %, about 10 to about 25 wt. %, about 12 to about 35 wt. %, about 12 to about 30 wt. %, about 12 to about 25 wt. %, about 12 to about 25 wt. %, or about 12 to about 20 wt. %, based on the total weight of the cleansing composition.

Alkyl Sulfosuccinates

Non-limiting examples of useful sulfosuccinates include those of formula (VII):

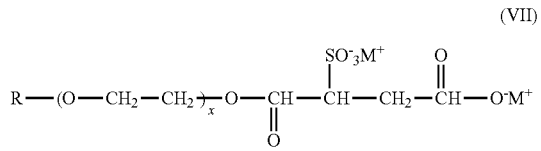

(VII)

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a mixture thereof. In some instances, disodium laureth sulfosuccinate is particularly preferred.

The total amount alkyl sulfosuccinate(s) in the cleansing compositions, if present, may range from about 1 to about 25 wt. %, based on the total weight of the cleansing composition. In some cases, the total amount of alkyl sulfosuccinate(s) in the cleansing composition may range from about 1 to about 20 wt. %, from about 1 to about 15 wt. %, from about 1 to about 10 wt. %, from about 1 to about 5 wt. %, from about 2 to about 25 wt. %, from about 2 to about 20 wt. %, from about 2 to about 15 wt. %, from about 2 to about 10 wt. %, or from about 2 to about 6 wt. %, based on the total weight of the cleansing composition.

Alkyl Sulfoacetates

Non-limiting examples of alkyl sulfacetates includes, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

The total amount of alkyl sulfosuccinate(s) in the cleansing compositions, if present, may range from about 0.1 to about 25 wt. %, based on the total weight of the cleansing composition. In some cases, the total amount of alkyl sulfosuccinate(s) in the cleansing composition ranges from about 0.1 to about 20, from about 0.1 to about 15 wt. %, from about 0.1 to about 10 wt. %, from about 0.1 to about 8 wt. %, from about 0.1 to about 5 wt. %, from about 0.5 to about 25 wt. %, from about 0.5 to about 20 wt. %, from about 0.5 to about 15 wt. %, from about 0.5 to about 10 wt. %, from about 0.5 to about 8 wt. %, from about 0.5 to about 5 wt. %, from about 1 to about 25 wt. %, from about 1 to about 20 wt. %, from about 1 to about 15 wt. %, from about 1 to about 10 wt. %, from about 1 to about 8 wt. %, or from about 1 to about 5 wt. %, based on the total weight of the cleansing composition.

Alkoxylated Monoacids

Non-limiting examples of alkoxylated monoacids include compounds corresponding to formula (VIII):

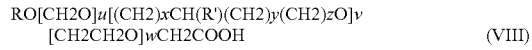

(VIII)

wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen, alkyl, and the sum of $x+y+z>0$;

Compounds corresponding to formula (VII) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (VII), R is linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof. In some cases, preferred ethoxylated acids include Oleth-10 Carboxylic Acid, Laureth-5 Carboxylic Acid, Laureth-11 Carboxylic Acid, and a mixture thereof.

The total amount of alkoxylated monoacids in the cleansing compositions, if present, may range from about 0.1 to about 40 wt. %, based on the total weight of the cleansing composition. In some cases, the total amount of alkoxylated monoacids in the cleansing compositions may range from about 0.1 to about 30 wt. %, about 0.1 to about 20 wt. %, about 0.1 to about 10 wt. %, about 0.1 to about 5 wt. %, about 0.5 to about 30 wt. %, about 0.5 to about 20 wt. %, about 0.5 to about 10 wt. %, about 1 to about 30 wt. %, about 1 to about 20 wt. %, about 1 to about 10 wt. %, or about 1 to 5 wt. %, based on the total weight of the cleansing composition.

Other Acyl Amino Acids (Amino Acid Surfactants)

Other acyl amino acid surfactants other than acyl taurates and acyl glutamates that may be used include, but are not limited to, amino acid surfactants based on alanine, arginine, aspartic acid, glycine, isoleucine, leucine, lysine, phenylalanine, serine, tyrosine, valine, sarcosine, and threonine.

Acyl Glycinates: Non-limiting examples of useful acyl glycinates include those of formula (IX):

(IX)

wherein R is an alkyl chain of 8 to 16 carbon atoms. Sodium is shown as the cation in the above formula (IX) but the cation may be an alkali metal ion such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

The total amount of acyl glycinates in the cleansing composition, if present, may vary but is typically from about 0.01 to about 25 wt. %, based on the total weight of the cleansing composition. In some instance, the total amount of acyl glycinates in the cleansing composition is from about 0.01 to about 20 wt. %, about 0.01 to about 15 wt. %, about 0.01 to about 10 wt. %, about 0.01 to about 5 wt. %, about 0.1 to about 25 wt. %, about 0.1 to about 20 wt. %, about 0.1 to about 15 wt. %, or about 0.1 to about 10 wt. %, or about 0.1 to about 5 wt. %, based on the total weight of the cleansing composition.

(ii) Alkyl Polyglucosides

Alkyl polyglucosides are a class of nonionic surfactants. The total amount of alkyl polyglucoside(s) in the cleansing compositions may vary but is typically from about 2 to about 25 wt. %, based on the total weight of the cleansing composition. In some instance, the total amount of alkyl polyglucoside(s) in the cleansing composition is from about 2 to about 20 wt. %, from about 2 to about 15 wt. %, from about 2 to about 10 wt. %, from about 5 to about 25 wt. %, from about 5 to about 20 wt. %, from about 5 to about 15 wt. %, or from about 5 to about 10 wt. %, based on the total weight of the cleansing composition. Most preferably, the non-ionic surfactant is about 5% to 30 wt. % of the cleaning composition.

Useful polyglucosides include alkyl polyglucosides having the following formula (X):

(X)

wherein R1 is an alkyl group having 8-18 carbon atoms;
R2 is an ethylene or propylene group;
Z is a saccharide group with 5 to 6 carbon atoms;
n is an integer from 0 to 10; and
x is an integer from 1 to 5.

Useful alkyl poly glucosides include arachidyl glucoside, C12-20 alkyl glucoside, cetearyl glucoside, lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

(iii) Amphoteric Surfactants

The total amount of amphoteric surfactant(s) in the cleansing compositions may vary but is typically from about 2 to about 25 wt. %, based on the total weight of the cleansing composition. In some instance, the total amount of amphoteric surfactant(s) in the cleansing composition is from about 2 to about 20 wt. %, from about 2 to about 15 wt. %, from about 2 to about 10 wt. %, from about 5 to about 25 wt. %, from about 5 to about 20 wt. %, from about 5 to about 15 wt. %, or from about 5 to about 10 wt. %, based on the total weight of the cleansing composition. Preferably, the amphoteric surfactant ranges from about 2% to 25 wt. %, and preferably it is one or more betaines, in particular, alkyl betaines, ranging from about 2% to 12 wt. %.

Useful amphoteric surfactants include betaines, alkyl betaines, alkyl sultaines, alkyl amphoacetates, alkyl amphoproprionates, and mixtures thereof. Non-limiting examples of useful amphoteric surfactants are provided below.

(iii-a) Betaines

Useful betaines include those of the following formulae (XIa-XId):

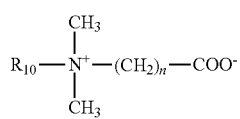
(XIa)

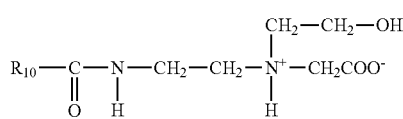
(XIb)

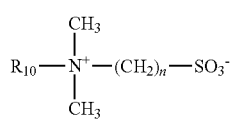
(XIc)

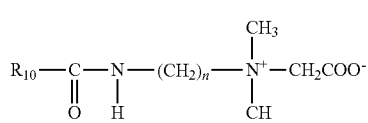
(XId)

wherein R10 is an alkyl group having 8-18 carbon atoms; and n is an integer from 1 to 3.

Particularly useful betaines include, for example, coca betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof. Typically, at least one betaine compound is selected from coco betaine, cocamidopropyl betaine, behenyl betaine, capryl/capramidopropyl betaine, and lauryl betaine, and mixtures thereof. Particularly preferred betaines include coco betaine and cocamidopropyl betaine.

The total amount of betaines in the cleansing composition, if present, may vary but is typically from about 2 to about 25 wt. %, based on the total weight of the cleansing composition. In some instance, the total amount of betaines(s) in the cleansing composition is from about 2 to about 20 wt. %, from about 2 to about 15 wt. %, from about 2 to about 10 wt. %, from about 5 to about 25 wt. %, from about 5 to about 20 wt. %, from about 5 to about 15 wt. %, or from about 5 to about 10 wt. %, based on the total weight of the cleansing composition.

(iii-b) Alkyl Sultaines

Non-limiting examples of alkyl sultaines include hydroxyl sultaines of formula (XII)

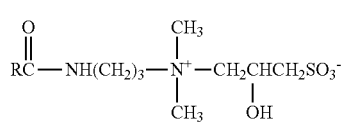
(XII)

wherein R is an alkyl group having 8-18 carbon atoms. More specific examples include, but are not limited to cocamidopropyl hydroxysultaine, lauryl hydroxysultaine, and a mixture thereof.

The total amount of alkyl sultaines in the cleansing composition, if present, may vary but is typically from about 0.01 to about 25 wt. %, based on the total weight of the cleansing composition. In some instance, the total amount of alkyl sultaines(s) in the cleansing composition is from about 0.01 to about 20 wt. %, about 0.01 to about 15 wt. %, about 0.01 to about 10 wt. %, about 0.01 to about 5 wt. %, about 0.1 to about 25 wt. %, about 0.1 to about 20 wt. %, about 0.1 to about 15 wt. %, or about 0.1 to about 10 wt. %, or about 0.1 to about 5 wt. %, based on the total weight of the cleansing composition.

(iii-c) Alkyl Amphoacetates and Alkyl Amphodiacetates

Useful alkyl amphoacetates and alkyl amphodiacetates include those of Formula (XIII) and (XIV):

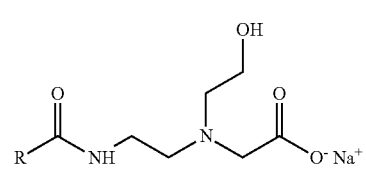
(XIII)

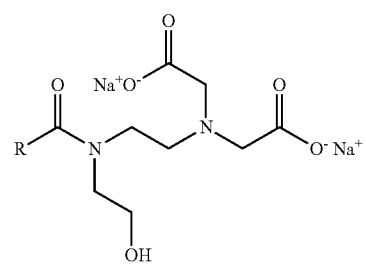
(XIV)

wherein R is an alkyl group having 8-18 carbon atoms. Sodium is shown as the cation in the above formulae above but the cation may be an alkali metal ion such as sodium or potassium, ammonium ions, or alkanolammonium ions such as monoethanolammonium or triethanolammonium ions. A more specific, but non-limiting example, is sodium lauroamphoacetate.

The total amount of alkyl amphoacetates and/or alkyl amphodiacetates in the cleansing composition, if present, may vary but is typically from about 0.01 to about 25 wt. %, based on the total weight of the cleansing composition. In some instance, the total amount of alkyl amphoacetates and/or alkyl amphodiacetates in the cleansing composition is from about 0.01 to about 20 wt. %, from about 0.01 to about 15 wt. %, from about 0.01 to about 10 wt. %, from about 0.01 to about 5 wt. %, from about 0.1 to about 25 wt. %, from about 0.1 to about 20 wt. %, from about 0.1 to about 15 wt. %, or from about 0.1 to about 10 wt. %, or about 0.1 to about 5 wt. %, based on the total weight of the cleansing composition.

(iii-d) Alkyl Amphopropionates

Non-limiting examples of alkyl amphopropionates include cocoamphopropionate, cornamphopropionatecaprylamphopropionate, cornamphopropionate, caproamphopropionate, oleoamphopropionate, isostearoamphopropionate, stearoamphopropionate, lauroamphopropionate, salts thereof, and a mixture thereof.

The total amount of alkyl amphopropionates in the cleansing composition, if present, may vary but is typically from about 0.01 to about 25 wt. %, based on the total weight of the cleansing composition. In some instance, the total amount of amphopropionates in the cleansing composition is from about 0.01 to about 20 wt. %, about 0.01 to about 15 wt. %, about 0.01 to about 10 wt. %, about 0.01 to about 5 wt. %, about 0.1 to about 25 wt. %, about 0.1 to about 20 wt. %, about 0.1 to about 15 wt. %, or about 0.1 to about 10 wt. %, or about 0.1 to about 5 wt. %, based on the total weight of the cleansing composition.

(iv) Miscellaneous Nonionic Surfactants

The cleansing compositions may optionally include one or more miscellaneous nonionic surfactants, i.e., one or more nonionic surfactants in addition to the alkyl polyglucosides and the amide surfactants discussed above. The total amount of miscellaneous nonionic surfactant(s), if present, can vary but may be in an amount of from about 0.01 to about 25 wt. %, based on the total weight of the cleansing composition. In some instance, the total amount of miscellaneous nonionic surfactant(s) in the cleansing composition is from about 0.01 to about 20 wt. %, from about 0.01 to about 15 wt. %, about 0.01 to about 10 wt. %, from about 0.01 to about 5 wt. %, from about 0.1 to about 25 wt. %, from about 0.1 to about 20 wt. %, from about 0.1 to about 15 wt. %, or from about 0.1 to about 10 wt. %, or about 0.1 to about 5 wt. %, based on the total weight of the cleansing composition.

The nonionic surfactant(s) can be, for example, selected from alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C6-C24) alkylpolyglycosides; N—(C6-C24)alkylglucamine derivatives, amine oxides such as (C10-C14)alkylamine oxides or N—(C10-C14)acylaminopropylmorpholine oxides; and mixtures thereof.

Such nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a C8-C24, preferably C12-C22, fatty acid or acids and alkoxylated derivatives thereof, preferably with a number of alkyleneoxide of from 10 to 200, and more preferably from 10 to 100; polyethylene glycol esters of a C8-C24, preferably C12-C22, fatty acid or acids and alkoxylated derivatives thereof, preferably with a number of alkyleneoxide of from 10 to 200, and more preferably from 10 to 100; sorbitol esters of a C8-C24, preferably C12-C22, fatty acid or acids and alkoxylated derivatives thereof, preferably with a number of alkyleneoxide of from 10 to 200, and more preferably from 10 to 100; sugar (sucrose, glucose, alkylglycose) esters of a C8-C24, preferably C12-C22, fatty acid or acids and alkoxylated derivatives thereof, preferably with a number of alkyleneoxide of from 10 to 200, and more preferably from 10 to 100; ethers of fatty alcohols; ethers of sugar and a C8-C24, preferably C12-C22, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of C8-C24 alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

Oil-Based Conditioning Agents

The oil-based conditioning agents of the present disclosure selected from squalane, glyceryl esters, esters other than glyceryl esters, natural oils, and mixtures thereof.

The total amount of oil-based conditioning agent(s) in the cleansing compositions can vary but is typically from about 0.1 to about 5 wt. %, based on the total weight of the cleansing composition. In some instances, the total amount of oil-based conditioning agent(s) in the cleansing compositions is from about 0.1 to about 8 wt. %, from about 0.1 to about 6 wt. %, from about 0.1 to about 5 wt. %, from about 0.1 to about 3 wt. %, from about 0.5 to about 10 wt. %, from about 0.5 to about 8 wt. %, from about 0.5 to about 6 wt. %, from about 0.5 to about 5 wt. %, or from about 0.5 to about 3 wt. %, based on the total weight of the cleansing composition.

Preferably, the conditioning agent is an oil-based and comprises 0.2% to 5 wt. % of the cleaning composition.

Squalane is a saturated branched chain hydrocarbon. It may be obtained by hydrogenation of shark liver oil or other natural oils, that conforms to the formula:

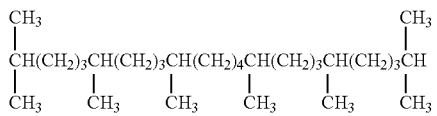

Squalane may also be described by its chemical name of 2,6,10,15,19,23-Hexamethyltetracosane or vegetable squalane.

Squalane is commercially available under the tradename of NEOSSANCE SQUALANE (vegetal or plant origin) from the company Amyris.

Suitable examples of glyceryl esters glyceryl ester (or (poly)glyceryl ester) include glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, or mixtures thereof. In certain embodiments, the at least one glyceryl ester may be chosen from polyglyceryl-4 isostearate, polyglyceryl-3 oleate, polyglyceryl-2 sesquioleate, triglyceryl diisostearate, diglyceryl monooleate, and tetraglyceryl monooleate.

In certain embodiments, the glyceryl ester may be chosen from polyglyceryl-3 caprate, polyglyceryl-4 caprate, glyceryl laurate, polyglyceryl-2 laurate, polyglyceryl-5 laurate, polyglyceryl-10 laurate, glyceryl myristate, glyceryl stearate, glyceryl undecylenate, glyceryl oleate, or mixtures thereof.

Suitable examples of esters or ester oils may be or include one or more diester oils. Non-limiting examples of diester oils include those chosen from diisostearyl malate, neopentyl glycol dioctanoate, dibutyl sebacate, di-C12-13 alkyl malate, dicetearyl dimer dilinoleate, dicetyl adipate, diisocetyl adipate, diisononyl adipate, diisostearyl dimer dilinoleate, diisostearyl fumarate, and mixtures thereof.

Esters may also be or include one or more triester oils. Examples of triester oils that may, optionally be used, include triethyl hexanoin, trimethylolpropane triethylhexanoate, triisostearin, trimethylolpropane triisostearate, etc. Tetraester oils include pentaerythrityl tetraethyl hexanoate, pentaerythrityl tetraisostearate, etc.

Esters may be or include one or more polyester oils. Non-limiting examples of polyester oils include polyglycerin fatty acid esters such as polyglyceryl-2 isostearate, polyglyceryl-2 diisostearate, polyglyceryl-2 triisostearate, polyglyceryl-2 tetraisostearate, etc.

The esters may also be high-viscosity ester oils such as those chosen from dipentaerythrityl hexa(hydroxystearate/stearate/rosinate), hydrogenated castor oil isostearate, hydrogenated castor oil dimer dilinoleate, (polyglyceryl-2 isostearate/dimer dilinoleate) copolymer, (phytosteryl/isostearyl/cetyl/stearyl/behenyl) dimer dilinoleate, bis(phytosteryl/behenyl/isostearyl) dimer dilinoleyl dimer dilinoleate, di(isostearyl/phytosteryl) dimer dilinoleate, dimer dilinoleyl hydrogenated rosin condensation product, dimer dilinoleyl diisostearate, dimer dilinoleyl dimer dilinoleate, di(cholesteryl/behenyl/octyldodecyl) lauroyl glutamate, di(octyldodecyl/phytosteryl/behenyl) lauroyl glutamate, myristoyl methylalanine (phytosteryl/decyl tetradecyl), (diglycerin/dilinoleate/hydroxystearate) copolymer, etc Other suitable examples of esters include polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, and a mixture thereof. Specific examples of the esters of fatty acids, and/or esters of fatty alcohols are cetyl palmitate, cetyl stearate, myristyl myristate, myristyl stearate, cetyl myristate, and stearyl stearate (a mixture of which is referred to as "cetyl esters")). ethyl palmitate, isopropyl palmitate, ethyl myristate, isocetyl stearate, 2-ethylhexyl isononanoate, isononyl isononanoate, isodecyl neopentanoate and isostearyl neopentanoate.

Plant oils that can be used in the compositions of the present invention include sunflower oil, corn oil, soybean oil, marrow oil, grapeseed oil, sesame seed oil, hazelnut oil, apricot oil, macadamia oil, castor oil, avocado oil, olive oil, rapeseed oil, coconut oil, wheatgerm oil, sweet almond oil, apricot oil, safflower oil, coconut oil, camellina oil, jojoba oil, shea butter oil, canola oil, cottonseed oil, palm oil, peanut oil, safflower oil, sesame oil, sunflower oil, linseed oil, palm kernel oil, mustard oil, pennycress oil, pistachio oil, poppy oil, pine oil, colza oil, cade oil, peach kernel oil, coffee bean oil, and mixtures thereof.

Thickening Agents

The hair-treatment compositions contain one or more thickening agents (also referred to as thickeners or viscosity modifying agents). Many thickening agents are water-soluble, and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

The total amount of thickening agent(s) in the cleansing compositions, if present, may vary but are typically in an amount of from about 0.5 to about 5 wt. %, from based on the total weight of the cleansing composition. In some instances, the total amount of thickening agent in the cleansing composition is from about 0.6 to about 4 wt. %, from about 0.7 to about 3 wt. %, based on the total weight of the cleansing composition.

Non-limiting examples of thickening agents include hydroxypropyl guar hydroxypropyltrimonium chloride, guar hydroxypropyltrimonium chloride, xanthan gum, guar gum, biosaccharide gum, cellulose, acacia Seneca gum, *sclerotium* gum, agarose, pechtin, gellan gum, hyaluronic acid. In some instances, the one or more thickening agents may include polymeric thickening agents, for example, those selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer.

In some instances, the thickening agent(s) are selected from carboxylic acid polymers (e.g., carbomer), crosslinked polyacrylate polymers, polyacrylamide polymers, polysaccharides, gums, and a mixture thereof. A more detailed description of various thickening agents is provided below.

Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

Crosslinked Polyacrylate Polymers

The compositions of the present disclosure can optionally contain crosslinked polyacrylate polymers useful as thickeners or gelling agents including both cationic and nonionic polymers.

Polyacrylamide Polymers

The compositions of the present disclosure can optionally contain polyacrylamide polymers, especially polyacrylamide polymers including substituted branched or unbranched polymers. Among these polyacrylamide polymers is the polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

Gums

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, biosacharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Optional, Other Conditioning Agents

Non-limiting examples of other conditioning agents other than the oil-based conditioning agents of the present disclosure include cationic conditioning polymers, non-silicone fatty compounds, silicones, cationic proteins, cationic protein hydrolysates, alkyl amines, and mixtures thereof.

The total amount of other conditioning agent(s) in the cleansing compositions, when present, can vary but is typically from about 0.1 to about 10 wt. %, based on the total weight of the cleansing composition. In some instances, the total amount of other conditioning agent(s) in the cleansing compositions is from about 0.1 to about 8 wt. %, from about 0.1 to about 6 wt. %, from about 0.1 to about 5 wt. %, from about 0.1 to about 3 wt. %, from about 0.5 to about 10 wt. %, from about 0.5 to about 8 wt. %, from about 0.5 to about 6 wt. %, from about 0.5 to about 5 wt. %, or from about 0.5 to about 3 wt. %, based on the total weight of the cleansing composition.

Cationic Conditioning Polymers

The cationic conditioning polymers may be homopolymers or formed from two or more types of monomers. The molecular weight of the polymer may be between 5,000 and 10,000,000, typically at least 10,000, and preferably in the range 100,000 to about 2,000,000. These polymers will typically have cationic nitrogen containing groups such as quaternary ammonium or protonated amino groups, or a mixture thereof.

The cationic charge density is suitably at least 0.1 meq/g, preferably above 0.8 or higher. In some instances, the cationic charge density does not exceed 3 meq/g, or does not exceed 2 meq/g. The charge density can be measured using the Kjeldahl method and can be within the above limits at the desired pH of use, which will in general be from about 3 to 9 and preferably between 4 and 8.

The cationic nitrogen-containing group will generally be present as a substituent on a fraction of the total monomer units of the cationic conditioning polymer. Thus when the polymer is not a homopolymer it can contain spacer non-cationic monomer units.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-C3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition.

Amine substituted vinyl monomers and amines can be polymerized in the amine form and then converted to ammonium by quaternization.

Suitable cationic amino and quaternary ammonium monomers include, for example, vinyl compounds substituted with dialkyl amincalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the C1-C3 alkyls, more preferably C1 and C2 alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably C1-C7 hydrocarbyls, more preferably C1-C3, alkyls.

The cationic conditioning polymers can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidine and 1-vinyl-3-methyl-imidazolium salt (e.g., Chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyl-diallyammonium chloride homopolymer and copolymers of acrylamide and dimethyldiallyammonium chloride (referred to as Polyquaternium-6 and Polyquaternium-7).

Other cationic conditioning polymers that can be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200.

Other cationic conditioning polymers that can be used include cationic guar gum derivatives, such as guar hydroxypropyltrimonium chloride.

Polyquaterniums include Polyquaternium-1 (ethanol, 2,2', 2"-nitrilotris-, polymer with 1,4-dichloro-2-butene and N,N, N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2- methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), and Polyquaternium-47 (terpolymer of acrylic acid, methacrylamidopropyl trimethylammonium chloride, and methyl acrylate).

In some instances, the cleansing compositions of the instant disclosure include one or more cationic conditioning polymers selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. In one particularly preferred embodiment, the cationic conditioning polymer(s) are selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, and a mixture thereof. In particular, a combination of two or more polyquaterniums can be particularly useful, for example, a combination of polyquaternium-7 and polyquaternium-10.

Non-Silicone Fatty Compounds

The term "non-silicone fatty compound" means a fatty compound that does not containing any silicon atoms (Si). Non-limiting examples of non-silicone fatty compounds include mineral oil (liquid paraffins or liquid petroleum), fatty alcohols, fatty acids, fatty alcohol derivatives, fatty acid derivatives (such as alkoxylated fatty acids) hydroxy-substituted fatty acids, waxes, lanolin, and a mixture thereof. Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

In some instances, the non-silicone fatty compounds include one or more waxes. The waxes generally have a melting point of from 35-120° C., at atmospheric pressure. Non-limiting examples of waxes in this category include for example, synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, sunflower seed wax (*Helianthus annuus*), acacia decurrents flower wax, or a mixture thereof.

In some instance, the non-silicone fatty compounds include one or more non-silicone oils. The term "oil" as used herein describes any material which is substantially insoluble in water. Suitable non-silicone oils include, but are not limited to, hydrocarbons, such as mineral oil and hydrogenated polyisobutene; fatty alcohols, such as octyldodecanol.

Mineral oils, such as liquid paraffin or liquid petroleum, or animal oils, such as perhydrosqualene orhydrocarbons derived by hydrogenation of squalene, squalane, 2,6,10,15,19,23-Hexamethyltetracosane, or Perhydrosqualene; Dodecahydrosqualene, can be used in the cleaning composition.

Silicones

The conditioning agent(s) of the cleansing compositions may optionally include one or more silicones. Nonetheless, as mentioned throughout the instant disclosure, in some instances the cleansing compositions are free or essentially free of silicones. In other words, one or more of the following silicones may be optionally included or optionally excluded from the cleansing compositions.

Silicones include, but are not limited to, polyorganosiloxanes, polyalkylsiloxanes, polyarylsiloxanes, polyalkarylsiloxanes, polyestersiloxanes, and a mixture thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane and a mixture thereof.

In some instances, the cleansing compositions include (or exclude) one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, and mixtures thereof.

The cleansing compositions may include (or exclude) one or more silicone oils, for example one or more non-phenyl silicone oils and/or one or more phenyl silicone oils. The silicone oil is preferably apolar. An "apolar silicone oil" is intended to denote a silicon oil that does not comprise any ionic or ionisable group(s), and preferably does not comprise any oxyalkylenated(C2-C4) unit(s) (preferably oxyethylene, oxypropylene), or glycerol unit(s).

Representative examples of non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups. It should be noted that "dimethicone" (INCI name) corresponds to a poly(dimethylsiloxane) (chemical name), which is particularly preferred in some instances.

The non-volatile non-phenyl silicone oil is preferably chosen from non-volatile dimethicone oils. In particular, these oils can be chosen from the following non-volatile oils:

polydimethylsiloxanes (PDMSs),
PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference ABIL WAX 9801 from Evonik Goldschmidt,
PDMSs comprising aliphatic groups, or functional groups such as hydroxyl, thiol and/or amine groups, [
polyalkylmethylsiloxanes substituted with functional groups such as hydroxyl, thiol and/or amine groups,
polysiloxanes modified with fatty acids, fatty alcohols or polyoxyalkylenes, and mixtures thereof.

Preferably, these non-volatile non-phenyl silicone oils are chosen from polydimethylsiloxanes; alkyl dimethicones and also PDMSs comprising aliphatic groups, in particular C2-C24 alkyl groups, and/or functional groups such as hydroxyl, thiol and/or amine groups.

The non-phenyl silicone oil may be chosen in particular from silicones of the following formula:

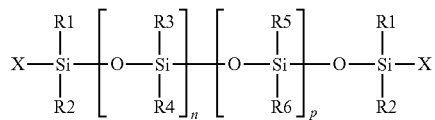

in which:
R1, R2, R5 and R6 are, together or separately, an alkyl radical containing 1 to 6 carbon atoms,
R3 and R4 are, together or separately, an alkyl radical containing from 1 to 6 carbon atoms, a vinyl radical, an amine radical or a hydroxyl radical,
X is an alkyl radical containing from 1 to 6 carbon atoms, a hydroxyl radical or an amine radical,
n and p are integers chosen so as to have a fluid compound, in particular of which the viscosity at 25° C. is between 9 centistokes (cSt) and 800 000 (cSt).

As non-volatile non-phenyl silicone oils which can be used according to the invention, mention may be made of those for which:
the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker,
the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning,
the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

Cationic Proteins and Cationic Protein Hydrolysates

Cationic proteins and cationic protein hydrolysates can be derived from animals, for example from collagen, milk, or keratin, from plants, for example from wheat, corn, rice, potatoes, soy, moringa, or almonds, from marine life forms, for example from fish collagen or algae, or from biotechnologically obtained protein hydrolysates. Those cationic protein hydrolysates may have a molecular weight from 100 to 25,000 dalton, from 250 to 5,000 dalton, or from 250 to 1000 dalton. Also to be understood as cationic protein hydrolysates are quaternized amino acids and mixtures thereof. Quaternization of the protein hydrolysates or of the amino acids is often carried out by means of quaternary ammonium salts such as, for example, N,N-dimethyl-N-(n-alkyl)-N-(2-hydroxy-3-chloro-n-propyl)ammonium halides. Typical examples that may be mentioned of cationic protein hydrolysates and derivatives according to the present invention are the products listed under the INCI names in the "International Cosmetic Ingredient Dictionary and Handbook," (seventh edition 1997, The Cosmetic, Toiletry, and Fragrance Association), which is incorporated herein by reference in its entirety. Non-limiting examples of Cationic protein hydrolysates include: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

Plant-based cationic proteins and cationic protein hydrolysates include but are not limited to those based on wheat, rice, corn, soy, almond, or moring, etc. Examples of cationic protein hydrolysates based on wheat include the commercial products Gluadin WQ, Gluadin WQT, and the Hydrotriticum series of the Croda company.

Miscellaneous Conditioning Agents

Many conditioning agents are known to those skilled in the art and need not be specifically listed herein. Nonetheless, a non-limiting example of miscellaneous conditioning agents include alkyl amines, such as mono-long alkyl amines, and ester oils. Mono-long alkyl amines include those having one long alkyl chain of preferably from 12 to 30 carbon atoms, more preferably from 16 to 24 carbon atoms, still more preferably from 18 to 22 alkyl group. Mono-long alkyl amines include mono-long alkyl amidoamines. Primary, secondary, and tertiary fatty amines are useful.

Non-limiting examples of alkyl amines include brassicamidopropyl dimethylamine, stearyl dimethyl amine, and stearamidopropyl dimethylamine.

Useful are tertiary amido amines having an alkyl group of from about 12 to about 22 carbons. Exemplary tertiary amido amines include: brassicamidopropyl dimethylamine, stearamidopropyldimethylamine, stearamidopropyldiethylamine, stearamidoethyldiethylamine, stearamido-ethyldimethylamine, palmitamidopropyldimethylamine, palmitamidopropyldiethylamine, palmitamidoethyldiethylamine, palmitamidoethyldimethylamine, behenamidopropyl-dimethylamine, behenamidopropyldiethylamine, behenamidoethyldiethylamine, behenamidoethyldimethylamine, arachidamidopropyldimethylamine, arach idamidopropyldiethylamine, arachidamidoethyldiethylamine, arachidamidoethyldimethylamine, diethylaminoethylstearamide.

These amines may be used in combination with acids such as 1-glutamic acid, lactic acid, hydrochloric acid, malic acid, succinic acid, acetic acid, fumaric acid, tartaric acid, citric acid, 1-glutamic hydrochloride, maleic acid, and mixtures thereof; more preferably 1-glutamic acid, lactic acid, and citric acid.

As already noted, the conditioning agent may be an ester oil. Ester oils include, but are not limited to, fatty esters having at least 10 carbon atoms. These fatty esters include esters derived from fatty acids or alcohols (e.g., monoesters, polyhydric alcohol esters, and di- and tri-carboxylic acid esters). The fatty esters hereof may include or have covalently bonded thereto other compatible functionalities, such as amides and alkoxy moieties (e.g., ethoxy or ether linkages, etc.)

The ester oil may for example be chosen from: monoesters comprising at least 18 carbon atoms and even more particularly containing between 18 and 40 carbon atoms in total, in particular monoesters of formula R1COOR2 in which R1 represents a linear or branched, saturated or unsaturated or aromatic fatty acid residue comprising from 4 to 40 carbon atoms and R2 represents a hydrocarbon-based chain that is in particular branched, containing from 4 to 40 carbon atoms, on condition that the sum of the carbon atoms of the radicals R1 and R2 is greater than or equal to 18, for instance Purcellin oil (cetostearyl octanoate), isononyl isononanoate, C12 to C15 alkyl benzoate, 2-ethylhexyl palmitate, octyldodecyl neopentanoate, 2-octyldodecyl stearate, 2-octyldodecyl erucate, isostearyl isostearate, C12-C15 alkyl benzoates such as 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate or 2-octyldodecyl myristate.

Preferably, they are esters of formula R1COOR2 in which R1 represents a linear or branched fatty acid residue comprising from 4 to 40 carbon atoms and R2 represents a hydrocarbon-based chain that is in particular branched, containing from 4 to 40 carbon atoms, R1 and R2 being such that the sum of the carbon atoms of the radicals R1 and R2 is greater than or equal to 18.

Water-Soluble Solvents

The cleansing compositions may optionally include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%.

The total amount of water-soluble solvents in the cleansing compositions, if present, may vary but are typically in an amount of about 0.01 to about 25 wt. %, based on the total weight of the cleansing composition. In some instances, the total amount of water-soluble solvents may be from about 0.01 to about 20 wt. %, about 0.01 to about 15 wt. %, about 0.01 to about 10 wt. %, about 0.01 to about 5 wt. %, about 0.1 to about 25 wt. %, about 0.1 to about 20 wt. %, about 0.1 to about 15 wt. %, about 0.1 to about 10 wt. %, about 0.1 to about 5 wt. %, based on the total weight of the cleansing composition.

Non-limiting examples of water-soluble solvents include, for example, organic solvents selected from glycerin, alcohols (for example, C1-12, C1-10, C1-8, or C1-4 alcohols), polyols (polyhydric alcohols), glycols, and a mixture thereof.

As examples of organic solvents, non-limiting mention can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

Film-Forming Polymers

The cleansing compositions of the instant disclosure do not require film-forming polymers (including anionic, amphoteric, and nonionic film-forming polymers). However, one or more filming-forming polymers may optionally be included. Therefore, the cleansing compositions may optionally include or exclude (may be free or essentially free of) one or more film forming polymers. Non-limiting examples of film-forming polymers that may optionally be included or excluded from the cleansing compositions include vinyl polymers, polyesters, polyamides, polyureas, and a mixture thereof. The one or more film-forming polymers may be polyethyleneimine, polylysine, polyvinyl alcohols, poly(hydroxyethyl (meth)acrylate), hydroxyalkylcelluloses, polyacrylic acid, polyvinylimidazoles, polypropyleneimines, polyallylamines, chitosan, carboxyalkylcelluloses, aminoalkylcelluloses, maleic, fumaric and/or itaconic acid or anhydride polymers, polyamidoamines, and a mixture thereof.

The one or more film-forming polymers may be copolymers of (meth)acrylic acid and of at least one ester monomer of linear, branched or cyclic (meth)acrylic acid and/or of at least one amide monomer of linear, branched or cyclic, mono- or disubstituted (meth)acrylic acid; (meth)acrylic acid/tert-butyl(meth)acrylate and/or isobutyl (meth)acrylate/ C1-C4 alkyl(meth)acrylate copolymers; (meth)acrylic acid/ ethyl acrylate/methyl methacrylate terpolymers and tetrapolymers; methyl methacrylate/butyl or ethyl acrylate/ hydroxyethyl or 2-hydroxypropyl acrylate or methacrylate/ (meth)acrylic acid tetrapolymers; copolymers of acrylic acid and of C1-C4 alkyl methacrylate; terpolymers of vinylpyrrolidone, of acrylic acid and of C1-20 alkyl methacrylate; amphoteric copolymers; vinyl esters of branched acids; vinyl esters of benzoic acid; copolymers of (meth)acrylic acid and of at least one olefinic monomer; copolymers of vinyl monoacid and/or of allylic monoacid; and a mixture thereof. In some cases, the one or more film-forming polymers include VP/dimethylaminoethylmethacrlate copolymer.

The cleansing compositions do not require silicones, film-forming polymers, and sulfate-based surfactants. Thus, any one or more (or all) of these may optionally be excluded from the cleansing compositions. In other words, the compositions may be free or essentially free of silicones and/or film-forming polymers and/or sulfate-based surfactants. Nonetheless, in some instances, one or more silicones and/or one or more film-forming polymers and/or one or more sulfate-based surfactants may optionally be included in the cleansing compositions.

In certain embodiments of the instant disclosure, the cleansing compositions include:
  a. up to 20 wt. % of one or more anionic surfactants selected from acyl taurate, acyl isethionate, acyl glutamate, salts and mixtures thereof.
  b. about 5% to 30 wt. % of one or more nonionic surfactants comprising alkyl polyglucosides (APG);
  c. about 2% to 25 wt. % of one or more amphoteric surfactants;
  d. about 0.2% to 5% of one or more oil conditioning agents selected from squalane, glyceryl esters, esters, and mixtures thereof;
  e. about 0.5% to 5% of one or more thickening agents comprising natural thickening agents;
  f. about 25% to 75% water;
    wherein all weight percentages are based on the total weight of the cleansing composition.

The surfactant combination, the conditioning agents, and the thickening agents in the embodiment above may be any of those described throughout the instant disclosure. Additionally, as noted above, the cleansing compositions do not require silicones, film-forming polymers, and sulfate-based surfactants. Thus, any one or more (or all) of these may optionally be excluded from the cleansing compositions. In other words, the compositions may be free or essentially free of silicones and/or film-forming polymers and/or sulfate-based surfactants. Nonetheless, in some instances, one or more silicones and/or one or more film-forming polymers and/or one or more sulfate-based surfactants may optionally be included in the cleansing compositions.

In yet further embodiments of the instant disclosure, the cleansing compositions include: about 15 to about 50 wt. % surfactants comprising—about 1% to 5 wt. % of acyl taurate; about 1% to 10 wt. % of acyl isethionate; optionally, about 0.1% to 3 wt. % of acyl glutamate; about 7% to 20 wt. % of APG; about 2% to 12 wt. % of one or more of one or more betaines; about 0.2% to 5% of one or more oil conditioning agents selected from squalane, glyceryl esters, esters, and mixtures thereof; about 0.5% to 5% of one or more thickening agents comprising cationic guar; wherein all weight percentages are based on the total weight of the cleansing composition.

In yet additional embodiments, the rinse-off cleansing compositions include: (a) about 1% to 5 wt. % of sodium methyl cocoyl taurate; (b) about 1% to 10 wt. % of sodium cocoyl isethionate; (c) optionally, about 0.1% to 3 wt. % of one or more of disodium cocoyl glutamate, sodium cocoyl glutamate, sodium stearoyl glutamate, and mixtures thereof; (d) about 7% to 20 wt. % of decyl glucoside; (e) about 2% to 12 wt. % of one or more of coco-betaine; (f) about 0.2% to 5% of one or more oil conditioning agents selected from squalane, glyceryl oleate, coco-caprylate/caprate, diisopropyl dimer dilinoleate, and mixtures thereof; (g) about 0.5% to 5% of hydroxypropyl guar hydroxypropyltrimonium chloride; wherein all weight percentages are based on the total weight of the cleansing composition.

The viscosity of the cleansing compositions discussed throughout the instant disclosure can vary but is often similar to that of typical cleansing, shampooing, and/or conditioning compositions. Accordingly, in some instances, the viscosity can be from about 2500 cP to about 15,000 cp at a temperature of 25° C. The viscosity measurements can be carried out, for example, using a Brooksfield viscometer/rheometer using a RV-3 Disk spindle at a speed of 5, 10, 15, and/or 20 rpm or using a Rheomat with an M4 spindle. An RVDV-II+Pro Viscometer with RheocalcT software may be employed for automated instrument control and data acquisition. The test temperature is maintained at 25° C. by using a Brookfield TC-502P Programmable Refrigerated Bath. From its original container, a sample is transferred into a 600 mL beaker and then tested.

In some cases, the viscosity is from about 2000 cP to about 20,000 cP, about 2000 cP to about 18,000 cP, about 2000 cP to about 15,000 cP, 2000 cP to about 15,000 cP, about 3000 cP to about 20,000 cP, about 3000 cP to about 18,000, about 3000 cP to about 15,000 cP, about 3000 cP to about 12,000 cP, or about 3000 cP to about 10,000 cP.

The cleansing compositions described throughout the instant disclosure may be in a variety of different forms, for example, gels, lotions, creams, milks, sprays, and the like. The cleansing compositions, however, are not typically in the form of an emulsion. Nonetheless, in some cases, the cleansing compositions may be in the form of a dispersion. Due to the cleansing and conditioning properties of the cleansing compositions, in some instances, the cleansing compositions may be designated as a "shampoo," a "conditioning shampoo," or an "all-in-one conditioning and shampooing composition." The cleansing compositions may also be a body wash or both a hair and body wash.

The cleansing compositions of the instant disclosure are particularly useful for cleansing and conditioning hair. Additionally, the cleansing compositions provide a variety of desirable cosmetic and styling benefits to the hair, for example, smoothness, detangling, and shine. Accordingly, the cleansing compositions are useful in methods for cleansing hair, methods of conditioning hair, and methods for imparting smoothness, detangling, and/or shine to hair. Accordingly, the instant disclosure encompasses methods for treating hair with the cleansing compositions of the instant disclosure. Such methods may include simply applying a cleansing composition of the instant disclosure to the hair.

In some cases, methods of using the cleansing compositions include shampooing and/or conditioning the hair with a cleansing composition of the instant disclosure. Such methods typically include applying an effective amount of a cleansing composition of the instant disclosure to the hair, allowing the cleansing composition to remain on the hair for a period of time, and subsequently rinsing the cleansing composition from the hair. The period of time for which the cleansing composition is allowed to remain on the hair is usually not long, e.g., not longer than about 5 minutes. Usually, the cleansing composition is merely allowed to remain on the hair for a period of time sufficient to incorporate the cleansing composition throughout the hair, for example, by lathering the composition throughout the hair using one's hands. The amount of time is sufficient for the cleansing composition to interact with the hair and any dirt, oil, contamination, etc., that may exist on the hair so that when rinsed, the dirt, oil, contamination, etc., can be effectively removed from the hair and the conditioning agents of the cleansing composition can interact with the hair to condition it. Thus, the cleansing composition may be allowed to remain on the hair for about 5 seconds to about 5 minutes, about 5 seconds to about 3 minutes, about 5 seconds to about 2 minutes, about 5 seconds to about 1 minute, about 30 seconds to about 5 minutes, or about 30 seconds to about 3 minutes.

As is common when using shampoo and/or conditioning compositions, the hair may be wetted or rinsed with water prior to application of a cleansing composition of the instant disclosure. Having water already in the hair can be helpful for creating lather when applying the cleansing compositions because the water interacts with the surfactants.

Implementation of the present disclosure is provided by way of the following examples. The examples serve to illustrate the technology without being limiting in nature.

The following examples serve to illustrate the embodiments of the disclosure without however exhibiting a limiting character. The Examples are intended to be non-restrictive and explanatory only, with the scope of the invention being defined by the claims. In these examples the amounts of the composition ingredients are given as weight percentages of active ingredients relative to the total weight of the composition.

EXAMPLE(S)

Examples 1A-1D and 2A-2D prepared generally as follows:

Solution/main kettle (MK): 1) APG, for non-limiting example, decyl glucoside, plus up to about 10% water; 2) pH adjustment, 5.0 to about 5.6, and misc., mix till dissolved. Begin heating to 75 deg. C.; 3) Add oil-based conditioning agent, for non-limited example pre-melted glyceryl oleate at high shear; 4) Add anionic surfactants, including for non-limiting example cocamide mipa, and sodium cocoyl isethionate at 40 deg. C. Mix till melted/homogenous; 5) once sodium cocoyl isethionate is fully incorporated, cool to 50 deg. C. and add remaining water; 6) Add SK* solution and continue cooling batch to 30 deg. C.; 7) add surfactants, including for non-limiting example, sodium methyl cocoyl taurate, disodium cocoyl glutamate (and) sodium cocoyl glutamate, and oil-based conditioning agent, including for non-limiting example squalane, glycerin, diisopropyl dimer dilinoleate, misc., mix between additions; 8) add amphoteric surfactant, for non-limiting example coco-betaine, and mix; 9) pH, about 5.0 to about 5.6.

*Thickening agent/side kettle (SK) solution: 1) Add about 20% of water; 2) Add preservative. Mix until dissolved; 3) Add thickening agents, for non-limiting example, hydroxypropyl guar hydroxypropyltrimonium chloride-mix until fully dispersed. Max about 1-2 hours; 4) bring temperature of Solution #2 to about 50 deg. C.

Examples 1A-1D—Rinse-Off Conditioning Shampoo

Four separate rinse-off shampoo compositions according to the disclosure were prepared by mixing the following ingredients in Table 1, as follows.

TABLE 1

| INCI US | Ex. 1-A | Ex. 1-B | Ex. 1-C | Ex. 1-D |
|---|---|---|---|---|
| | | Wt. % | | |
| SODIUM METHYL COCOYL TAURATE | 2.22 | 2.22 | 2.22 | 2.22 |
| SODIUM COCOYL ISETHIONATE | 4.0 | 4.0 | 4.0 | 4.0 |
| DISODIUM COCOYL GLUTAMATE | 0.81 | 0.81 | 0.81 | 0.81 |
| SODIUM COCOYL GLUTAMATE | 0.19 | 0.19 | 0.19 | 0.19 |
| DECYL GLUCOSIDE | 7.95 | 7.95 | 7.95 | 7.95 |
| COCO-BETAINE | 2.1 | 2.1 | 2.1 | 2.1 |
| SQUALANE | 0.3 | 0.3 | 0.3 | 0.3 |
| GLYCERYL OLEATE | 1 | 0.50 | 0.50 | 0.50 |
| DIISOPROPYL DIMER DILINOLEATE | — | — | — | 0.5 |
| COCO-CAPRYLATE/CAPRATE | — | — | 0.5 | — |
| GLYCERIN | 2.0 | 2.0 | 2.0 | 2.0 |
| COCAMIDE MIPA | 1.0 | 1.0 | 1.0 | 1.0 |
| HYDROXYPROPYL GUAR HYDROXYPROPYLTRIMONIUM CHLORIDE | 0.7 | 1.0 | 0.7 | 0.7 |
| WATER | Q.S.100 | Q.S.100 | Q.S.100 | Q.S.100 |
| pH Adjuster | ≤1 | ≤1 | ≤1 | ≤1 |
| Miscellaneous (one or more of vitamins, protein or hydrolyzed protein, preservatives, salts, plant extracts, plant extract derivatives, fragrances, anti-static agents, etc.) | <2.0 | <2.0 | <2.0 | <2.0 |

(1) commercially available under the tradename of NEOSSANCE SQUALANE (vegetal or plant origin) from the company Amyris The cosmetic properties of compositions 1A-1D, which comprise the subject cleansing composition described herein, were evaluated. The compositions were found to have dense, lush, creamy foam, with a viscosity that would be typical of a shampoo composition, but with higher oil loading. This was surprising because generally the inclusion of high oil load would be expected to negatively affect these cosmetic properties of the shampoo composition. Thus, the components of the conditioning system synergistically worked together in order to avoid such a negative effect on the composition properties.

Compositions 1A-1D were then applied to wet hair, lathered, and the hair was rinsed, combed, dried, and styled. The compositions lathered very well and coated the hair nicely. The compositions rinsed easily from the hair. After rinsing, the ease of detangling the wet hair was superior, and provided a nourishing effect from the high oil load.

The above examples demonstrate that the synergistic combination of the surfactant combination and high oil load, provide unexpectedly superior cosmetic properties to the rinse-off composition, as well as unexpectedly superior cleansing and conditioning properties which leave the hair in surprisingly excellent condition.

Examples 2A-2D—Rinse-Off Conditioning Shampoo

Four separate rinse-off shampoo compositions according to the disclosure were prepared by mixing the following ingredients in Table 2, as follows.

TABLE 2

| INCI US | Ex. 2-A | Ex. 2-B | Ex. 2-C | Ex. 2-D |
|---|---|---|---|---|
| | | Wt. % | | |
| SODIUM METHYL COCOYL TAURATE | 2.22 | 2.22 | 1.48 | 2.22 |
| SODIUM COCOYL ISETHIONATE | 4.0 | 4.0 | 5.0 | 4.0 |
| DISODIUM COCOYL GLUTAMATE | — | — | — | 0.81 |
| SODIUM COCOYL GLUTAMATE | — | — | — | 0.19 |

TABLE 2-continued

| INCI US | Ex. 2-A | Ex. 2-B | Ex. 2-C | Ex. 2-D |
|---|---|---|---|---|
| | | Wt. % | | |
| SODIUM STEAROYL GLUTAMATE | 1.00 | 2.00 | — | — |
| DECYL GLUCOSIDE | 7.95 | 7.95 | 5.3 | 7.95 |
| COCO-BETAINE | 2.1 | 2.1 | 3. | 2.1 |
| SQUALANE (1) | 0.3 | 0.3 | — | 0.3 |
| GLYCERYL OLEATE | 0.5 | 0.5 | 0.5 | 0.5 |
| COCO-CAPRYLATE/CAPRATE | — | — | 0.3 | — |
| GLYCERIN | 2.0 | 2.0 | 2.0 | 2.0 |
| COCAMIDE MIPA | 1.0 | 1.0 | 2.0 | 1.0 |
| LAURYL LACTYL LACTATE | — | — | — | 0.1 |
| HYDROXYPROPYL GUAR HYDROXYPROPYLTRIMONIUM CHLORIDE | 0.7 | 0.7 | 1.2 | 0.7 |
| WATER | Q.S.100 | Q.S.100 | Q.S.100 | Q.S.100 |
| pH Adjuster | ≤1 | ≤1 | ≤1 | ≤1 |
| Miscellaneous (one or more of vitamins, protein or hydrolyzed protein, preservatives, salts, plant extracts, plant extract derivatives, fragrances, anti-static agents, etc.) | <2.0 | <2.0 | <2.0 | <2.0 |

(1) commercially available under the tradename of NEOSSANCE SQUALANE (vegetal or plant origin) from the company Amyris.

Examples 3A-3B: Comparative Hair Color Compositions

Two separate comparative rinse-off shampoo compositions were prepared by mixing the ingredients in Table 3 below, and compared to Examples 1A-1D and 2A-2D above. The following comparative hair color compositions were prepared in the same manner as described in Examples 1 and 2.

TABLE 3

| US INCI ingredient name | Ex 3-A | EX 3-B |
|---|---|---|
| | Wt. % | |
| SODIUM LAUROYL METHYL ISETHIONATE | 3.4 | — |
| SODIUM LAUROYL SARCOSINATE | 0.06 | 3.0 |
| SODIUM COCOYL ISETHIONATE | — | 5.0 |
| COCO-BETAINE | — | 2.7 |
| DECYL GLUCOSIDE | 6.0-7.0 | 6.0-7.0 |
| CATIONIC GUAR | — | 0.5 |
| COCAMIDE MIPA | 1.0 | — |
| GLYCERYL OLEATE | 1.0-2.0 | 1.0-2.0 |
| GUMs | 0.6 | — |
| MISC | </=3.0 | </=3.0 |
| WATER | QS 100 | QS 100 |

Comparative data—Testing report vs the reference/commercials is attached.

TABLE 4

| | Ex. 3A-3B | Ex. 1A-1D, Ex. 2A-2D |
|---|---|---|
| Foam Height (avg) | 60.33 mm | 87.56 mm |
| Foam MBA (avg) - 20 sec | 929 um | 1170 um |
| Detangling | ++ | +++ |
| Cosmeticity | ++ | +++ |
| Stability (4 W 45 C.) | +++ | ++++ |
| Stability (8 W 45 C.) | + | ++++ |

Compositions 3A-3B were applied to wet hair, lathered, and the hair was rinsed, combed, dried, and styled, as above. The cosmetic properties of compositions Ex. 1A-1D and Ex. 2A-2D, which comprise the subject cleansing composition described herein, were evaluated, and compared with those of Ex. 3A-3B. Compositions Ex 1A-1D and Ex. 2A-2D demonstrated greater foam height and MBA averages when compared to Ex. 3A-3B, and greater stability at 4 W and 8 W. Ex. 1A-1D and Ex. 2A-2D provided a nourishing effect from the high oil load, providing unexpectedly superior cosmetic properties to the rinse-off composition, as well as unexpectedly superior cleansing and conditioning properties. Ex. 1A-1D and Ex. 2A-2D were found to provide improved cosmeticity and detangling to the hair as compared to Ex. 3A-3B, on information and belief, due to high natural oil/high oil loading content—which is a technical challenge for natural essentially sulfate free and/or sarcosinate free shampoos.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−5% of the indicated number.

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention. Similarly, the compositions may include less than 0.5 wt. %, less than 0.1 wt. %, less than 0.05 wt. %, or less than 0.01 wt. %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A rinse-off cleansing composition with high oil load, the composition comprising:
    (a) up to 20 wt. % of one or more anionic surfactants selected from acyl isethionates, salts thereof, and mixtures thereof;
    (b) one or more alkyl polyglucosides;
    (c) one or more amphoteric surfactants;
    (d) about 0.2 to about 5 wt. % of coco-caprylate/caprate;
    (e) one or more thickening agents;
    (f) one or more cationic conditioning polymers selected from quaternized hydroxyethyl celluloses;
        wherein the cleansing composition comprises less than 1 wt. % of sulfate-based surfactants, and,
        all weight percentages are based on the total weight of the cleansing composition.

2. The cleansing composition of claim 1, wherein the one or more alkyl polyglucosides and the coco-caprylate/caprate are in a weight ratio greater than 1.

3. The cleansing composition of claim 1, wherein the one or more alkyl polyglucosides and the coco-caprylate/caprate are in a weight ratio ranging from about 3 up to about 60.

4. The cleansing composition of claim 1, wherein the one or more alkyl polyglucosides and the coco-caprylate/caprate are in a weight a ratio ranging from about 5 up to about 20.

5. The cleansing composition of claim 1, wherein the one or more alkyl polyglucosides are selected from lauryl glucoside, octyl glucoside, decyl glucoside, and coco glucoside.

6. The cleansing composition of claim 1, wherein the one or more amphoteric surfactants are selected from betaines, alkyl betaines, alkyl sultaines, alkyl amphoacetates, and alkyl amphoprorionates.

7. The cleaning composition of claim 1, wherein the one or more anionic surfactants are selected from sodium cocoyl isethionate, sodium lauroyl isethionate, and sodium lauroyl methyl isethionate.

8. The cleansing composition of claim 1 being free from polymeric acrylates.

9. The cleansing composition of claim 1 comprising one or more silicones.

10. The cleansing composition of claim 9, wherein the one or more silicones are selected from dimethicone and amodimethicone.

11. A rinse-off cleansing composition with high oil load, the composition comprising:
(a) up to 20 wt. % of one or more anionic surfactants selected from acyl isethionates, salts thereof, and mixtures thereof;
(b) about 5 to 30 wt. % of one or more alkyl polyglucosides;
(c) about 2 to 25 wt. % of one or more amphoteric surfactants;
(d) about 0.2 to about 5 wt. % of coco-caprylate/caprate;
(e) about 0.5 to about 5 wt. % of one or more thickening agents;
(f) about 25 to about 75 wt. % of water; and
(g) about 0.1 to about 3 wt. % of one or more cationic conditioning polymers selected from quaternized hydroxyethyl celluloses;
wherein the cleansing composition comprises less than 1 wt. % of sulfate-based surfactants, and
all weight percentages are based on the total weight of the cleansing composition.

12. The cleansing composition of claim 11 being free from polymeric acrylates.

13. The cleansing composition of claim 11, wherein the one or more alkyl polyglucosides and the coco-caprylate/caprate are in a weight ratio greater than 1.

14. The cleansing composition of claim 11, wherein the one or more alkyl polyglucosides and the coco-caprylate/caprate are in a weight ratio ranging from about 3 up to about 60.

15. The cleaning composition of claim 11, wherein the one or more anionic surfactants are selected from sodium cocoyl isethionate, sodium lauroyl isethionate, and sodium lauroyl methyl isethionate.

16. The cleansing composition of claim 11 comprising one or more silicones.

17. The cleansing composition of claim 16, wherein the one or more silicones are selected from dimethicone and amodimethicone.

18. A method for cleansing the hair and/or scalp, the method comprising applying to the hair and/or scalp, and subsequently rinsing off, the rinse-off cleansing composition of claim 1.

19. A method for cleansing the hair and/or scalp, the method comprising applying to the hair and/or scalp, and subsequently rinsing off, the rinse-off cleansing composition of claim 11.

* * * * *